United States Patent [19]

Chodnekar et al.

[11] 4,390,540
[45] Jun. 28, 1983

[54] IMIDAZOQUINAZOLINES HAVING PHARMACEUTICAL ACTIVITY

[75] Inventors: Madhukar S. Chodnekar, Seltisberg; Ado Kaiser, Lausen; Frank Kienzle, Flüh, all of Switzerland

[73] Assignee: Hoffmann-La Roche Inc., Nutley, N.J.

[21] Appl. No.: 292,315

[22] Filed: Aug. 12, 1981

[30] Foreign Application Priority Data

Aug. 15, 1980 [CH] Switzerland .................. 6192/80
May 27, 1981 [CH] Switzerland .................. 3483/81

[51] Int. Cl.³ .................. A61K 31/505; C07D 487/04
[52] U.S. Cl. .................. 424/251; 544/247; 544/250
[58] Field of Search .................. 544/250, 247; 424/251

[56] References Cited

U.S. PATENT DOCUMENTS 3,883,524  5/1975  Wolf et al. .................. 424/251 X
4,183,932  1/1980  Yamamoto et al. .................. 424/251
4,256,748  3/1981  Chodnekar et al. .................. 424/251

FOREIGN PATENT DOCUMENTS 55-55188  4/1980  Japan .................. 424/251
56-29591  3/1981  Japan .................. 424/251

OTHER PUBLICATIONS

Rodighiero, et al., Biochem. Biophys. Acta., 217, pp. 40–49 (1970).
Bantick, et al., J. Med. Chem., vol. 19, No. 6, pp. 817–821 (1976).
Cannon, et al., J. Med. Chem., vol. 23, No. 1, pp. 1–5 (1980).
Chakrabarti, et al., J. Med. Chem., vol. 23, No. 8, pp. 878–884 (1980).
Temple, Jr., et al., J. Med. Chem., vol. 23, No. 11, pp. 1188–1198 (1980).
Coppola, et al., J. Org. Chem. vol. 41, No. 5, pp. 825–831 (1976).

*Primary Examiner*—Donald G. Daus
*Assistant Examiner*—Diana G. Rivers
*Attorney, Agent, or Firm*—Jon S. Saxe; Bernard S. Leon; William G. Isgro

[57] ABSTRACT

Imidazoquinazolines of the formula

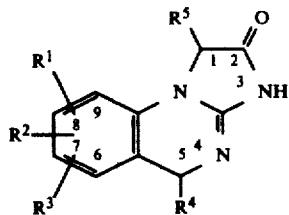

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms taken together are methylenedioxy or ethylenedioxy; and $R^4$ and $R^5$ are hydrogen or $C_{1-4}$-alkyl, and their tautomers, as well as their physiologically compatible acid addition salts, are described.

The compounds of formula I inhibit the aggregation of the blood platelets, as well as gastric acid secretion, and have activity on the circulatory system.

12 Claims, No Drawings

IMIDAZOQUINAZOLINES HAVING PHARMACEUTICAL ACTIVITY

BRIEF SUMMARY OF THE INVENTION

The invention relates to imidazoquinazolines of the formula

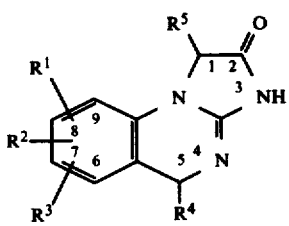

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms taken together are methylenedioxy or ethylenedioxy; and $R^4$ and $R^5$ are hydrogen or $C_{1-4}$-alkyl,
their tautomers, as well as their physiologically compatible acid addition salts.

DETAILED DESCRIPTION OF THE INVENTION

The invention comprises imidazoquinazolines of the formula

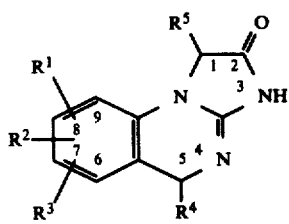

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms taken together are methylenedioxy or ethylenedioxy; and $R^4$ and $R^5$ are hydrogen or $C_{1-4}$-alkyl,
and their tautomers.

As used herein, the expression $C_{1-4}$-alkyl or $C_{1-4}$-alkoxy denotes straight-chain or branched-chain groups, such as, methyl, ethyl, propyl, isopropyl, butyl and the like, and the corresponding alkoxy groups. The expression $C_{2-5}$-alkoxyalkyl denotes straight-chain or branched-chain groups such as methoxymethyl. The expression halogen denotes chlorine, bromine, fluorine and iodine.

Preferred among the compounds of formula I, there are those wherein $R^1$ and $R^2$ are hydrogen, halogen, $C_{1-4}$-alkyl or $C_{1-4}$-alkoxy in the 6- and 7-position, especially those wherein $R^1$ and $R^2$ are hydrogen, chlorine, bromine, methyl or methoxy in the 6- and 7-position and $R^3$ is hydrogen. Compounds of formula I wherein $R^1$ is 6-chloro, $R^2$ is 7-chloro and $R^3$ is hydrogen are especially preferred.

Further, there are preferred the compounds of formula I wherein $R^4$ and $R^5$ are methyl or hydrogen.

Examples of such preferred compounds are:
6,7-Dichloro-4,5-dihydroimidazo[1,2-a]quinazolin-2(1H)-one,
6-chloro-4,5-dihydroimidazo[1,2-a]quinazolin-2(1H)-one, their tautomers, as well as their physiologically compatible acid addition salts.

Examples of compounds of formula I are:
7-Bromo-6-methyl-4,5-dihydroimidazo[1,2-a]quinazolin-2(1H)-one,
6,7-dimethyl-4,5-dihydroimidazo[1,2-a]quinazolin-2(1H)-one,
7-chloro-4,5-dihydroimidazo[1,2-a]quinazolin-2(1H)-one,
7-methoxy-4,5-dihydroimidazo[1,2-a]quinazolin-2(1H)-one,
7-chloro-6-methyl-4,5-dihydroimidazo[1,2-a]quinazolin-2(1H)-one,
7-methyl-4,5-dihydroimidazo[1,2-a]quinazolin-2(1H)-one,
6-methyl-4,5-dihydroimidazo[1,2-a]quinazolin-2(1H)-one,
4,5-dihydroimidazo[1,2-a]quinazolin-2(1H)-one,
6,7,8-trimethoxy-4,5-dihydroimidazo[1,2-a]quinazolin-2(1H)-one,
6-chloro-7-methoxy-4,5-dihydroimidazo[1,2-a]quinazolin-2(1H)-one,
8-chloro-4,5-dihydroimidazo[1,2-a]quinazolin-2(1H)-one,
9-methyl-4,5-dihydroimidazo[1,2-a]quinazolin-2(1H)-one,
6,7-dimethoxy-4,5-dihydroimidazo[1,2-a]quinazolin-2(1H)-one,
1-methyl-6-chloro-7-methoxy-4,5-dihydroimidazo[1,2-a]quinazolin-2(1H)-one,
5-methyl-7-methoxy-4,5-dihydroimidazo[1,2-a]quinazolin-2(1H)-one,
6-methyl-7-methoxy-4,5-dihydroimidazo[1,2-a]quinazolin-2(1H)-one,
5-methyl-4,5-dihydroimidazo[1,2-a]quinazolin-2(1H)-one,
6,7-dichloro-1-methyl-4,5-dihydroimidazo[1,2-a]quinazolin-2(1H)-one,
8-methyl-4,5-dihydroimidazo[1,2-a]quinazolin-2(1H)-one, and the corresponding tautomers thereof.

The invention also relates to a process for the preparation of the aforementioned compounds as well as pharmaceutical preparations based on the aforementioned compounds.

Examples of physiologically compatible or pharmaceutically acceptable acid addition salts are mineral acid salts, especially hydrochlorides, hydrobromides, sulfates and phosphates.

The compounds of formula I can exist in various tautomeric forms. The invention is, therefore, not limited to compounds of formula I depicted earlier, but also includes their tautomers, for example those of formulas

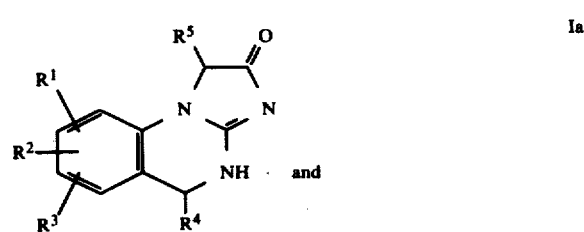

and

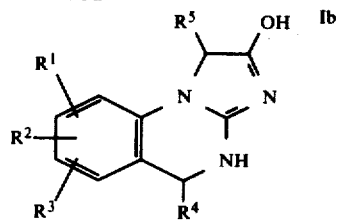

wherein $R^1$-$R^5$ are as previously described. The compounds of formula I and their tautomers wherein $R^4$ and/or $R^5$ are different from hydrogen can, moreover, exist as racemates or in optically active form, all of these forms are also part of the invention.

The compounds of formula I and their tautomers, as well as salts of such compounds, can be prepared in accordance with the invention by treating a compound of the formula

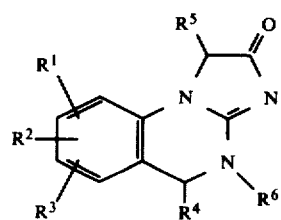

wherein $R^1$-$R^5$ are as previously described and $R^6$ is a benzyl group optionally ring-substituted by $C_{1-4}$-alkyl or $C_{1-4}$-alkoxy,
with an acid and isolating a resulting compound of formula I or a tautomer thereof in this form or in the form of a physiologically compatible or pharmaceutically acceptable acid addition salt.

A mineral acid, such as orthophosphoric acid, is conveniently used as the acid. The reaction can be carried out at a temperature in the range of from room temperature to 150° C., preferably in the range of from 100° to 120° C., preferably in the presence of anisole.

The compounds of formula II can be prepared by reacting a compound of the formula

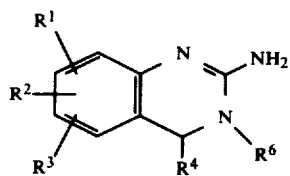

with an ester of the formula

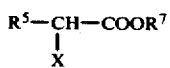

wherein $R^1$-$R^6$ are as previously described, $R^7$ is $C_{1-4}$-alkyl and X is chlorine, bromine or iodine, preferably iodine,
conveniently in an organic solvent, such as dimethylformamide or acetonitrile, at a temperature up to the reflux temperature of the reaction mixture, preferably in the presence of an inorganic base, such as potassium carbonate.

The compounds of formula III can be prepared according to the following Reaction Scheme wherein $R^1$-$R^4$ and $R^6$ are as previously described in analogy to the process for the preparation of 3-substituted-2-amino-3,4-dihydroquinazoline derivatives starting from 2-nitro benzyl halides described in Chem.Pharm.Bull 28 (1980) 1357-1364:

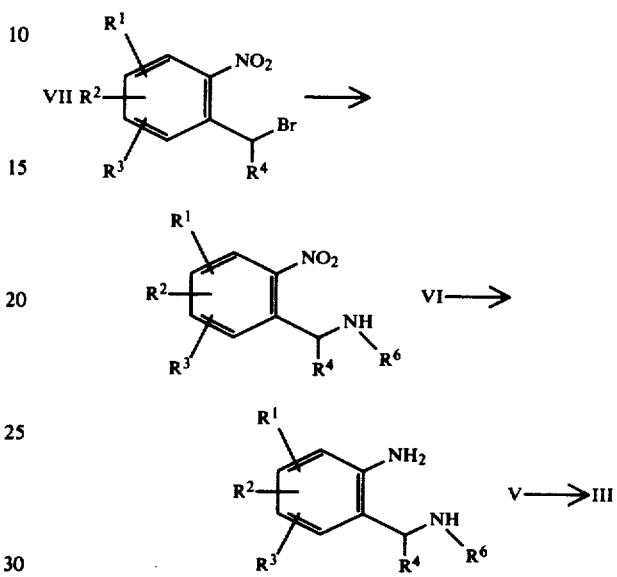

The compounds of formula I, their tautomers and physiologically compatible or pharmaceutically acceptable salts of such compounds can be used as medicaments. For example, they inhibit the aggregation of the blood platelets and can, therefore, be used for the prevention of thromboses. Further, they inhibit gastric acid secretion and can, therefore, be used for the treatment and prevention of gastric ulcers. Moreover, they are active on the circulatory system. Thus, for example, they exhibit positive inotropic activity without producing a substantial tachycardia, and can be used for the treatment and prophylaxis of cardiac insufficiency and cardiac failure.

The compounds of formula I and their tautomers can be used as medicaments; for example, in the form of pharmaceutical preparations which contain them or their salts in admixture with an organic or inorganic inert carrier material which is suitable for enteral, percutaneous or parenteral administration, such as, for example, water, gelatin, gum arabic, lactose, starch, magnesium stearate, talc, vegetable oils, polyalkyleneglycols and the like. The pharmaceutical preparations can be made up in solid form, for example, as tablets, dragees, suppositories or capsules, in semi-solid form, for example, as salves, or in liquid form, for example, as solutions, suspensions or emulsions. The pharmaceutical preparations can be sterilized and/or can contain adjuvants, such as preserving, stabilizing, wetting or emulsifying agents, salts for varying the osmotic pressure or buffers. They can also contain still other therapeutically valuable substances. The oral administration of the compounds in accordance with the invention is preferred. For adult hosts, that is, warm-blooded animals, there comes into consideration an oral daily dosage in the range of from 0.1 to 30 mg/kg and a parenteral daily dosage in the range of from 0.01 to 10 mg/kg. The preferred dosage range for compounds administered for the prevention of thromboses is from 1 to 10 mg for an adult per day and is 5 to 30 mg for an adult per day for compounds administered in the treatment of cardiac insufficiency, depending or individual requirements and route of administration.

The aggregation-inhibiting activity was demonstrated according to the aggregometer method of BORN [Nature 194, 927 (1962) and MICHAL and BORN [Nature 231, 220 (1971)]. The maximum aggregation velocity was taken as the test parameter, and the effective concentration ($EC_{50}$) was ascertained from dosage-activity curves.

Human platelet-rich plasma was obtained by centrifugation from citrated venous blood. The experiments were carried out with suspensions of the test substances in 0.9% sodium chloride. 0.18 ml of citrate plasma was treated with a 10 μl suspension of the test compounds and incubated at 37° C. for 10 minutes, whereupon the aggregation was initiated by the addition of 10 μl of a suspension of collagen fibrils.

| Collagen-Induced Blood Platelet Aggregation | |
| --- | --- |
| Compound | $EC_{50}$ (μM) |
| 6-Chloro-4,5-dihydroimidazo[1,2-a]quinazolin-2(1H)one hydrochloride | 12.3 |
| 7-Bromo-6-methyl-4,5-dihydroimidazo[1,2-a]quinazolin-2(1H)-one hydrochloride | 35.0 |

The experimental procedure described hereinafter was used to determine the gastric acid secretion-inhibiting activity. More specifically, the pylorus of female rats, which had received no food for 24 hours, but which had received water ad libitum, is ligatured under slight ether narcosis in accordance with Shay et al. [Gastroenterology 5, 43 (1945)]. Immediately thereafter the substance to be tested is administered intraduodenally to the animals. Four hous later the animals are killed, the volume and the acidity of their gastric juice are determined and the values obtained are compared with those of control animals which were treated similarly, but which received no test substance. The ED 50 is that dosage of test substance which brings about a 50% decrease in volume (ED 50 volume) or acidity (ED 50 acidity) of the gastric juice in the treated animals compared with the control animals. The following values were obtained for 6-chloro-4,5-dihydroimidazo[1,2-a]quinazolin-2(1H)-one hydrochloride: ED 50 volume = 15 mg/kg intraduodenally and ED 50 acidity = 10 mg/kg intraduodenally.

The positive inotropic activity was measured after the oral administration of the test substances to conscious sheep dogs. For this purpose, the animals are provided with an implanted pressure-telemetry system, whereby the pressure receiver is fixed in the left ventricle. The left ventricular pressure is sent from the animal via the implanted radio transmitter and received via a suitable antenna and receiving system, demodulated and amplified. By differentiation of the ascending side of the left ventricular pressure (LVP), there is calculated the maximum pressure increase rate ($dLVP/dt_{max}$) which represents the contractility parameter. Simultaneously, the heart frequency is recorded via a cardiotachograph. Under inotropy there are indicated the percentage variation ($\Delta\%$) of $dLVP/dt_{max}$ and the duration of activity in hours (Hrs.). Under tachycardia there are indicated the percentage variations of the heart frequency ($\Delta\%$) after administration of the test substance and the duration of activity in hours (Hrs.). The results are reproduced in the Table which follows:

TABLE

| Compound | Dosage mg/kg | Inotropy Δ% | Inotropy Hrs | Heart frequency Δ% | Heart frequency Hrs. |
| --- | --- | --- | --- | --- | --- |
| 6-Chloro-4,5-dihydroimidazo[1,2-a]quinazolin 2(1H)-one hydrochloride | 10 | +78 | 7 | +77 | 6 |
| 6,7-Dimethyl-4,5-dihydroimidazo[1,2-a]quinazolin-2(1H)-one hydrochloride | 10 | +18 | 6 | +3 | 6 |
| 7-Chloro-4,5-dihydroimidazo[1,2-a]quinazolin-2(1H)-one hydrochloride | 10 | +17 | 3.5 | +13 | 3 |
| 7-Methoxy-4,5-dihydroimidazo[1,2-a]quinazolin-2(1H)-one hydrochloride | 10 | +67 | 7 | +50 | 6.5 |
| 6,7-Dichloro-4,5-dihydroimidazo[1,2-a]quinazolin-2(1H)-one hydrochloride | 1 | +44 | 7.5 | +22 | 7 |
| 6-Methyl-4,5-dihydroimidazo[1,2-a]quinazolin-2(1H)-one hydrochloride | 1 | +15 | 2 | −7 | 3.5 |
| | 3 | +32 | 4.5 | −12 | 5 |
| 9-Methyl-4,5-dihydroimidazo[1,2-a]quinazolin-2(1H)-one hydrochloride | 1 | +27 | 2.5 | −19 | 5.5 |
| | 3 | +18 | 6.5 | −8 | 6 |
| 7-Methyl-4,5-dihydroimidazo[1,2-a]quinazolin-2(1H)-one hydrochloride | 3 | +33 | 2 | +6 | 1 |
| 4,5-Dihydroimidazo[1,2-a]quinazolin-2(1H)-one hydrochloride | 3 | +79 | 4 | +4 | 2.5 |
| 6-Chloro-7-methoxy-4,5-dihydroimidazo[1,2-a]quinazolin-2(1H)-one hydrochloride | 1 | +10 | 1 | +47 | 5 |
| | 3 | +32 | 7 | +20 | 6 |
| | 10 | +60 | 7 | +45 | 7 |
| 7-Chloro-6-methyl-4,5-dihydroimidazo[1,2-a]quinazolin-2(1H)-one hydrochloride | 1 | +27 | 6 | +4 | 5 |
| | 3 | +7 | 1 | +6 | 3 |
| | 10 | +50 | 6 | +31 | 6 |
| 7-Bromo-6-methyl-4,5-dihydroimidazo[1,2-a]quinazolin-2(1H)-one hydrochloride | 1 | +8 | 2.5 | +10 | 4 |
| | 3 | +16 | 5.5 | 0 | 4 |
| | 10 | +120 | 8 | +59 | 8 |
| 6,7-Dichloro-1-methyl-4,5-dihydro[1,2-a]quinazolin-2(1H)-one hydrochloride | 3 | +48 | 8 | +16 | 8 |

The Examples which follow further illustrate the invention. All temperatures are in degrees centigrade unless otherwise stated.

EXAMPLE 1

6-Chloro-4,5-dihydroimidazo[1,2-a]quinazolin-2(1H)-one

A solution of 0.1 mol of 6-chloro-4-(p-methoxybenzyl)-5H-imidazo[1,2-a]quinazolin-2(1H)-one in 1.2 l of 85% phosphoric acid and 60 ml of anisole is heated at 120° with stirring for 5 hours. Then, the mixture is cooled, poured into 6 l of ice/water and made alkaline with concentrated ammonia solution. The precipitate, which is 6-chloro-4,5-dihydroimidazo[1,2-a]quinazolin-2(1H)-one, is removed by filtration and washed with water. Yield: 60–80%.

In order to prepare the hydrochloride, the free base is dissolved in warm ethanol with the addition of an equivalent amount of 25% hydrochloric acid and left to crystallize-out by slowly cooling; m.p. 305° (decomposition).

The starting material can be prepared as follows:

A solution of 100 g of 2-chloro-6-nitrobenzyl bromide in 600 ml of methanol is added dropwise at room temperature to a solution of 200 g of p-methoxybenzylamine in 600 ml of methanol. After 5 hours, most of the methanol evaporates, and the residue is poured into ice/water. The precipitate of 2-chloro-4'-methoxy-6-nitrodibenzylamine is removed by filtration. By dissolution in methanol/hydrochloric acid the hydrochloride is prepared. The formed salt is recrystallized from methanol/ethyl acetate; m.p. 183°–186°.

A solution of 100 g of 2-chloro-4'-methoxy-6-nitrodibenzylamine hydrochloride in 1 l of ethanol, with the addition of 50 ml of triethylamine, is hydrogenated in the presence of Raney-nickel. Then, the catalyst is removed by filtration, the filtrate is evaporated, the residue is suspended in 300 ml of aqueous ammonia and extracted with ether. The ether solution is evaporated, and the residual 2-amino-6-chloro-4'-methoxydibenzylamine is converted by dissolution in methanol and treatment with hydrochloric acid into the monohydrochloride; m.p. 127°–129°.

55 g of 2-amino-6-chloro-4'-methoxydibenzylamine are dissolved in 1 l of dioxane and stirred with 21.5 g of cyanogen bromide for 4 days at room temperature. Then, the mixture is diluted with 1 l of ether and 47.5 g of 2-amino-5-chloro-3,4-dihydro-3-(p-methoxybenzyl)-quinazoline hydrobromide (m.p. 245°–247°) are removed by filtration.

A solution of 0.15 mol of 2-amino-5-chloro-3,4-dihydro-3-(p-methoxybenzyl)-quinazoline hydrobromide in 800 ml of dimethylformamide is treated with 0.18 mol of ethyl iodoacetate and 0.2 mol of potassium carbonate and stirred at room temperature for 18 hours. Then, the mixture is stirred at 90° for an additional 5 hours, cooled and poured into 5 l of ice/water. The precipitated product, 6-chloro-4-(p-methoxybenzyl)-5H-imidazo[1,2-a]quinazolin-2(1H)-one, is removed by filtration and washed well with water. In order to prepare the hydrochloride, the product is recrystallized from ethanol/hydrochloric acid; m.p. 230° (decomposition).

EXAMPLE 2

In an analogous manner to Example 1, the following compounds of formula 1 are prepared:

from 6,7-dimethyl-4-(p-methoxybenzyl)-5H-imidazo[1,2-a]quazolin-2(1H)-one, m.p. of the hydrochloride 225°–226° (decomposition), there is prepared 6,7-dimethyl-4,5-dihydroimidazo[1,2-a]quinazolin-2(1H)-one hydrochloride, m.p. <300° (decomposition);

from 7-chloro-4-(p-methoxybenzyl)-5H-imidazo[1,2-a]quinazolin-2(1H)-one, m.p. of the hydrochloride 228°–229° (decomposition), there is prepared 7-chloro-4,5-dihydroimidazo[1,2-a]quinazolin-2(1H)-one hydrochloride, m.p. 295°–297° (decomposition);

from 7-methoxy-4-(p-methoxybenzyl)-5H-imidazo[1,2-a]quinazolin-2(1H)-one, m.p. of the hydrochloride 244°–245° (decomposition), there is prepared 7-methoxy-4,5-dihydroimidazo[1,2-a]quinazolin-2(1H)-one hydrochloride, m.p. 290° (decomposition);

from 6,7-dichloro-4-(p-methoxybenzyl)-5H-imidazo[1,2-a]quinazolin-2(1H)-one, m.p. of the hydrochloride 237°–238° (decomposition), there is prepared 6,7-dichloro-4,5-dihydroimidazo[1,2-a]quinazolin-2(1H)-one hydrochloride, m.p. <300° (decomposition); p0 from 6-methyl-4-(p-methoxybenzyl)-5H-imidazo[1,2-a]quinazolin-2(1H)-one, m.p. of the hydrochloride 240°–245° (decomposition), there is prepared 6-methyl-4,5-dihydroimidazo[1,2-a]quinazolin-2(1H)-one hydrochloride, m.p. <300° (decomposition);

from 9-methyl-4-(p-methoxybenzyl)-5H-imidazo[1,2-a]quinazolin-2(1H)-one, m.p. of the hydrochloride 228°–229° (decomposition), there is prepared 9-methyl-4,5-dihydroimidazo[1,2-a]quinazolin-2(1H)-one hydrochloride, m.p. 270°–272° (decomposition);

from 8-chloro-4-(p-methoxybenzyl-5H-imidazo[1,2-a]quinazolin-2(1H)-one, m.p. of the hydrochloride 231°–234° (decomposition), there is prepared 8-chloro-4,5-dihydroimidazo[1,2-a]quinazolin-2(1H)-one hydrochloride, m.p. <300° (decomposition);

from 6,7,8-trimethoxy-4-(p-methoxybenzyl)-5H-imidazo[1,2-a]quinazolin-2(1H)-one, m.p. of the hydrochloride 230°–231° (decomposition), there is prepared 6,7,8-trimethoxy-4,5-dihydroimidazo[1,2-a]quinazolin-2(1H)-one hydrochloride, m.p. 250° (decomposition);

from 6,7-dimethoxy-4-(p-methoxybenzyl)-5H-imidazo[1,2-a]quinazolin-2(1H)-one, m.p. of the hydrochloride 255°–256° (decomposition), there is prepared 6,7-dimethoxy-4,5-dihydroimidazo[1,2-a]quinazolin-2(1H)-one hydrochloride, m.p. 258° (decomposition);

from 7-methyl-4-(p-methoxybenzyl)-5H-imidazo[1,2-a]quinazolin-2(1H)-one, m.p. of the hydrochloride 236°–237° (decomposition), there is prepared 7-methyl-4,5-dihydroimidazo[1,2-a]quinazolin-2(1H)-one hydrochloride, m.p. <300° (decomposition);

from 4-(p-methoxybenzyl)-5H-imidazo[1,2-a]quinazolin-2(1H)-one, m.p. of the hydrochloride 226°–227° (decomposition), there is prepared 4,5-dihydroimidazo[1,2-a]quinazolin-2(1H)-one hydrochloride, m.p. <300° (decomposition);

from 6-chloro-7-methoxy-4-(p-methoxybenzyl)-5H-imidazo[1,2-a]quinazolin-2(1H)-one, m.p. of the hydrochloride 262° (decomposition), there is prepared 6-chloro-7-methoxy-4,5-dihydroimidazo[1,2-a]quinazolin-2(1H)-one hydrochloride, m.p. 290° (decomposition);

from 7-chloro-6-methyl-4-(p-methoxybenzyl)-5H-imidazo[1,2-a]quinazolin-2(1H)-one, m.p. of the hydrochloride 231°-232° (decomposition), there is prepared
7-chloro-6-methyl-4,5-dihydroimidazo[1,2-a]quinazolin-2(1H)-one hydrochloride, m.p. <300° (decomposition);
from 7-bromo-6-methyl-4-(p-methoxybenzyl)-5H-imidazo[1,2-a]quinazolin-2(1H)-one, m.p. of the hydrochloride 252°-254° (decomposition), there is prepared
7-bromo-6-methyl-4,5-dihydroimidazo[1,2-a]quinazolin-2(1H)-one hydrochloride, m.p. <300° (decomposition);
from 1-methyl-6-chloro-7-methoxy-4-(p-methoxybenzyl)-5H-imidazo[1,2-a]quinazolin-2(1H)-one, m.p. of the hydrochloride 252° (decomposition), there is prepared
1-methyl-6-chloro-7-methoxy-4,5-dihydroimidazo[1,2-a]quinazolin-2(1H)-one hydrochloride, m.p. 250° C. (decomposition);
from 6,7-dichloro-1-methyl-4-(p-methoxybenzyl)-5H-imidazo[1,2a]quinazolin-2(1H)-one, m.p. of the hydrochloride 212°-214°, there is prepared
6,7-dichloro-1-methyl-4,5-dihydroimidazo[1,2-a]quinazolin-2(1H)-one hydrochloride, m.p. 284°-289°; and
from 5-methyl-4-(p-methoxybenzyl)-5H-imidazo[1,2-a]quinazolin-2(1H)-one, m.p. of the hydrochloride 227°-228°, there is prepared
5-methyl-4,5-dihydroimidazo[1,2-a]quinazolin-2(1H)-one hydrochloride, m.p. 280° (decomposition).

EXAMPLE 3

The following compounds are prepared in a manner analogous to Example 1:
5-Methyl-7-methoxy-4,5-dihydroimidazo[1,2-a]quinazolin-2(1H)-one;
6-methyl-7-methoxy-4,5-dihydroimidazo[1,2-a]quinazolin-2(1H)-one, m.p. of the hydrochloride 285°-287° (decomposition); and
8-methyl-4,5-dihydroimidazo[1,2-a]quinazolin-2(1H)-one, m.p. of the hydrochloride 300° (decomposition).

EXAMPLE 4

Tablets of the following composition are prepared in the usual manner:

| | |
|---|---|
| 6-Chloro-4,5-dihydroimidazo[1,2-a]quinazolin-2(1H)-one hydrochloride | 185.0 mg |
| Lactose | 15.0 mg |
| Maize starch | 37.5 mg |
| Water-soluble polyvinylpyrrolidone | 10.0 mg |
| Magnesium stearate | 2.5 mg |
| Total weight per tablet | 250.0 mg |

EXAMPLE 5

Interlocking gelatin capsules of the following composition are prepared in the usual manner:

| | |
|---|---|
| 6-Chloro-4,5-dihydroimidazo[1,2-a]quinazolin-2(1H)-one hydrochloride | 200.0 mg |
| Water-soluble polyvinylpyrrolidone | 2.0 mg |
| Maize starch | 43.0 mg |
| Talc | 4.5 mg |
| Magnesium stearate | 0.5 mg |
| Total weight per capsule | 250.0 mg |

EXAMPLE 6

A parenteral solution of the following composition is prepared in the usual manner:

| | |
|---|---|
| 6-Chloro-4,5-dihydroimidazo[1,2-a]quinazolin-2(1H)-one hydrochloride | 115.0 mg |
| Glycerinformal | 2.4 ml |
| Water | 4.0 ml |

We claim:
1. A compound of the formula

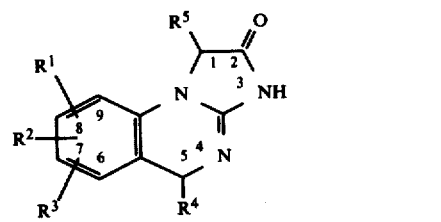

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms together are methylenedioxy or ethylenedioxy; and $R^4$ and $R^5$ are hydrogen or $C_{1-4}$-alkyl, its tautomers, as well as its pharmaceutically acceptable acid addition salts.

2. A compound in accordance with claim 1, wherein $R^1$ and $R^2$ are hydrogen, halogen, $C_{1-4}$-alkyl or $C_{1-4}$-alkoxy in the 6- and 7-position and $R^3$ is hydrogen.

3. A compound in accordance with claim 2, wherein $R^1$ and $R^2$ are hydrogen, chlorine, bromine, methyl or methoxy in the 6- and 7-position and $R^3$ is hydrogen.

4. A compound in accordance with claim 3, wherein $R^1$ is 6-chloro, $R^2$ is 7-chloro and $R^3$ is hydrogen.

5. A compound in accordance with claim 1, 2, 3 or 4, wherein $R^4$ and $R^5$ are hydrogen or methyl.

6. A compound in accordance with claim 1, 6,7-dichloro-4,5-dihydroimidazo[1,2-a]quinazolin-2(1H)-one, its tautomers, or a pharmaceutically acceptable acid addition salt thereof.

7. A compound in accordance with claim 1, 6-chloro-4,5-dihydroimidazo[1,2-a]quinazolin-2(1H)-one, its tautomers, or a pharmaceutically acceptable acid addition salt thereof.

8. A compound, in accordance with claim 1, selected from the group consisting of:
7-Bromo-6-methyl-4,5-dihydroimidazo[1,2-a]quinazolin-2(1H)-one,
6,7-dimethyl-4,5-dihydroimidazo[1,2-a]quinazolin-2(1H)-one,
7-chloro-4,5-dihydroimidazo[1,2-a]quinazolin-2(1H)-one,
7-methoxy-4,5-dihydroimidazo[1,2-a]quinazolin-2(1H)-one,
7-chloro-6-methyl-4,5-dihydroimidazo[1,2-a]quinazolin-2(1H)-one,
7-methyl-4,5-dihydroimidazo[1,2-a]quinazolin-2(1H)-one,
6-methyl-4,5-dihydroimidazo[1,2-a]quinazolin-2(1H)-one 4,5-dihydroimidazo[1,2-a]quinazolin-2(1H)-one, 6,7,8-trimethoxy-4,5-dihydroimidazo[1,2-a]quinazolin-2(1H)-one, 6-chloro-7-methoxy-4,5-dihydroimidazo[1,2-a]quinazolin-2(1H)-one, 8-chloro-4,5-dihydroimidazo[1,2-a]quinazolin-2(1H)-one, 9-methyl-4,5-dihydroimidazo[1,2-a]quinazolin-2(1H)-one, 6,7-dimethoxy-4,5-dihydroimidazo[1,2-a]quinazolin-2(1H)-one, 1-methyl-6-chloro-7-methoxy-4,5-dihydroimidazo[1,2-a]quinazolin-2(1H)-one, 5-methyl-7-methoxy-4,5-dihydroimidazo[1,2-a]quinazolin-2(1H)-one, 6-methyl-7-methoxy-4,5-dihydroimidazo[1,2-a]quinazolin-2(1H)-one, 5-methyl-4,5-dihydroimidazo[1,2-a]quinazolin-2(1H)-one, 6,7-dichloro-1-methyl-4,5-dihydroimidazo[1,2-a]quinazolin-2(1H)-one, 8-methyl-4,5-dihydroimidazo[1,2-a]quinazolin-2(1H)-one, the corresponding tautomers thereof or a pharmaceutically acceptable acid addition salt thereof.

9. A pharmaceutical composition containing a compound of the formula

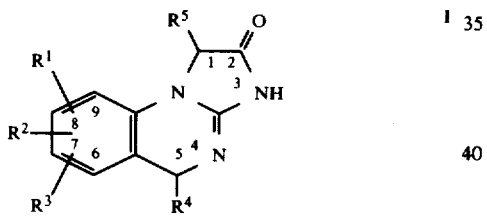

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms together are methylenedioxy or ethylenedioxy; and $R^4$ and $R^5$ are hydrogen or $C_{1-4}$-alkyl,
and an inert carrier material.

10. A method of inhibiting blood platelet aggregation which comprises administering an effective amount of a compound of the formula

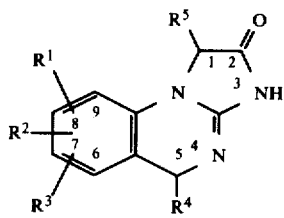

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms together are methylenedioxy or ethylenedioxy; and $R^4$ and $R^5$ are hydrogen or $C_{1-4}$-alkyl.

11. A method of inhibiting gastric acid secretion which comprises administering an effective amount of a compound of the formula

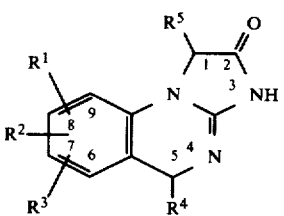

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms together are methylenedioxy or ethylenedioxy; and $R^4$ and $R^5$ are hydrogen or $C_{1-4}$-alkyl.

12. A method of producing positive inotropic activity which comprises administering an effective amount of a compound of the formula

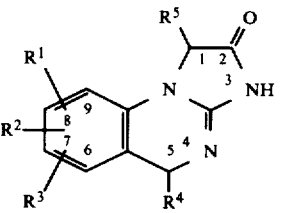

wherein $R^1$, $R^2$ and $R^3$ are hydrogen, halogen, $C_{1-4}$-alkyl, $C_{1-4}$-alkoxy or $C_{2-5}$-alkoxyalkyl; or two of $R^1$, $R^2$ and $R^3$ on adjacent carbon atoms together are methylenedioxy or ethylenedioxy; and $R^4$ and $R^5$ are hydrogen or $C_{1-4}$-alkyl.

* * * * *